United States Patent [19]

Sethofer et al.

[11] Patent Number: 5,172,256
[45] Date of Patent: Dec. 15, 1992

[54] LIQUID CRYSTAL VARIABLE COLOR DENSITY LENS AND EYE PROTECTIVE DEVICES INCORPORATING THE SAME

[76] Inventors: Nicholas L. Sethofer, 1184 Runnymede Dr., San Jose, Calif. 95117; Eric R. Henderson, deceased, late of Boulder Creek, Calif., by Donna R. James, Deputy Public Administrator

[21] Appl. No.: 293,696

[22] Filed: Jan. 5, 1989

Related U.S. Application Data

[63] Continuation-in-part of Ser. No. 145,463, Jan. 19, 1988, abandoned.

[51] Int. Cl.$^5$ ............... G02F 1/1337; G02F 1/1333; G02F 1/137; G02F 1/13
[52] U.S. Cl. ........................... 359/77; 359/83; 359/85; 359/90; 359/98; 359/106
[58] Field of Search ............... 350/331 R, 347 V, 349, 350/350 R, 346, 332; 359/77, 83, 90, 98, 106, 85

[56] References Cited

U.S. PATENT DOCUMENTS

| | | | |
|---|---|---|---|
| 4,323,473 | 4/1982 | Sethofer | 350/349 |
| 4,323,504 | 4/1982 | Sethofer | 350/349 |
| 4,495,083 | 1/1985 | Imazeki et al. | 359/98 |
| 4,550,980 | 11/1985 | Shingu | 359/98 |
| 5,026,505 | 6/1991 | Kaneko et al. | 359/98 |

FOREIGN PATENT DOCUMENTS

| | | | |
|---|---|---|---|
| 0026013 | 2/1986 | Japan | 350/349 |
| 0026021 | 2/1986 | Japan | 350/349 |
| 121420 | 6/1987 | Japan | |

OTHER PUBLICATIONS

Kawarada et al., "An Improved Positive Contrast Guest-Host Type Display Using Nematic-Cholesteric Phase Change", Conference: *International Electron Devices Meeting*, Dec. 1981, pp. 301–304.

Saunders, "New Photostable Anthraquinone Dyes with High Order Parameters", *Proceedings of the SID*, vol. 24/2, 1983, pp. 159–162.

*Primary Examiner*—Janice A. Howell
*Assistant Examiner*—Anita Pellman Gross
*Attorney, Agent, or Firm*—Michael J. Hughes

[57] ABSTRACT

The present invention is a novel and improved variable color/variable density optical system (10) adapted for use in a variety of lens and window applications. The preferred device embodying the invention is a novel optical sunlight protective device (12) incorporating a liquid crystal color lens, a photodetecting sensor component and circuit (18) and oscillating/driving electronic circuit (70), all of the present invention and incorporated in an appropriate frame (24). The lens element (b 14) includes plastic housing (40,42) of a curved shape complementary to any desired fashion design and, a liquid crystalline medium (58) of the novel phase change guest-host type. Combination of the lens construction, homeotropic surface alignment (48, 50) and aforementioned liquid crystal/dye complex brings about the clear, optical distortion-free variable color transmission with broad ranges of color density with incorporated protection against ultraviolet radiation. Two conductive layers of lens elements (44, 46) are connected to the driving electronics (70) of the present invention such that variations in light intensity on the photo-detecting sensor component and circuit (18) result in final corresponding variations in the alignment of liquid crystalline complex (58), thus altering the light transmissivity of the lens element (14). Eyewear products incorporating the optical device (10) function effectively under both bright sunshine and overcast or foggy conditions, including all intermediate and changing light conditions, thus making them useful over a wide range of applications.

17 Claims, 9 Drawing Sheets

LIQUID CRYSTAL VARIABLE COLOR DENSITY LENS AND EYE PROTECTIVE DEVICES INCORPORATING THE SAME

This is a continuation-in-part of copending application Ser. No. 07/145,463 filed on Jan. 19, 1988, now abandoned.

TECHNICAL FIELD

The present invention relates generally to optical devices and more particularly to automatic and variable optical color density lenses adapted to respond to ambient light conditions. The inventive lens provides eye protection against sunlight or other light sources, where the same lens, having ability to change color density and even color itself, may be used under varying light conditions such as heavy overcast or under other minimal lighting conditions with still efficient light transmission as well as in bright conditions. The invention uses a novel action modification of the optical liquid crystal device known as phase change guest-host in conjunction with a novel plastic device fabrication process and novel electronic system, including a photo-detecting and a oscillating/driver systems. These modifications in the liquid crystal/dye complex and in the device construction were invented to accommodate substantial differences of optical lens operation requirements as compared to the operation of the state-of-the-art information displays. Also the functions of electronic photo-detecting and driving systems were invented to accommodate proper operation of this particular lens. The preferred embodiment of the present invention is intended for use in the vicinity of a person's eyes, such as in ski goggles, and sun glasses, etc., and is useful in providing eye protection for light in both the visible and ultraviolet spectra and in providing either or both gradual and rapid changes, depending on the selected control mechanism, in the color density of the lens.

PRIOR ART

Shortcomings of the pair of lenses with fixed color and a color density within an optical sunglass protective device are obvious. Therefore, numerous attempts have been made to design a device that would provide a variable density and color changes for human eye protection.

Variable color density of the lens can be provided by a pair of colored polarized elements, as described by Land in U.S. Pat. No. 4,099,858; by Eloranta et al. in U.S. Pat. No. 4,119,369 and by Nannini in U.S. Pat. No. 4,386,832 or by a selective optical filter as described by Carreau et al. in U.S. Pat. No. 4,229,082. Even though such an action would be highly desirable, shortcomings of aforementioned systems are quite obvious as they require either continuous manual adjustments with every change, or selective areas of vision within the lens for different light intensity conditions. One problem that also effects the usefulness of this method is lack of a broad variety of colors and hues in polarizers.

There are also optical lenses available which provide color density darkening and fading. These devices are called photochromic lenses and their function is based upon the admixture of light sensitive silver halides into optical materials. These silver halides molecules are optically transmissive, in molecular form. However, in a photochemical reaction induced by radiant energy, these molecules physically separate under the effect of bright sunlight, ionizing to silver metal and halide ions. The silver metal in the lens reflects and absorbs light, reducing transmissivity and thus causing the lens to darken. This process is reversible under normal conditions and photochromic lenses can be described as light shutters.

However, these useful products have their considerable shortcomings, as well. First, the complete darkening of the photochromic lens takes 3-5 minutes while the time needed for this lens to return to its full transmission is usually between 10 to 20 minutes. Second, the photochromic lens is driven mainly by ultraviolet radiation, resulting in the fact that it does not function well while driving, as the automobile windshield absorbs a great portion of the ultraviolet radiation. As another specific limitation, this lens displays a distinctively blue tint under overcast conditions in higher altitudes, causing visual flattening of the snow covered terrain. It is also well known that photochromic molecules function best when embedded in glass lenses, while plastic versions can become unreasonably slow and may also have considerably shorter functional lifetimes than glass lenses. This means that best of available photochromic glasses are glass, which is typically heavy to wear, fragile, and expensive.

Considerable progress in the design of an effective light shutter has been further achieved by combination of the liquid crystal and electronics technologies. There are several designs of liquid crystal shutters described in the prior art. One type is based on the teaching of Fergason in U.S. Pat. No. 3,731,986 and describing what is now known as twisted nematic (further TN) light modulating display. Construction of such a display, including use of polarizing sheets (positioned in parallel or crossed fashion) is well known to those skilled in the art. Numerous patents, connected with improved display performance and/or new liquid crystal materials and mixtures, were granted in this particular field, since. Recently, several teachings concerning utilization of TN technology in eyewear products have been disclosed.

Examples of such applications are described by Harsch in U.S. Pat. No. 4,039,254, by Gordon in U.S. Pat. No. 4,237,557 and 4,241,286, by Tong-Shen in U.S. Pat. No. 4,491,390 and by Eggenschwiller et al. in U.S. Pat. No. 4,620,322; all of hereinabove devices being modifications of lenses with electronic designs for welding helmet assemblies. Another utilization of the liquid crystal and electronics technologies for an effective light shutter in a recording apparatus is described by Ohta et al. in U.S. Pat. Nos. 4,614,954 and 4,641,156. Application of TN technology in the field of personal eyewear with a specifically designed electronic circuit is described by Belgorod in U.S. Pat. No. 4,279,474.

An advantage of the all aforementioned liquid optical devices is their ability to provide changes from rather low transmission level (maximum of 40-45%) to almost complete opacity (up to 99.9%) within a fraction of a second. The liquid crystal devices described in aforementioned patents are of the twisted nematic type where light density changes are provided by action of two polarizers and a layer of liquid crystal. However, the useful utilization of this particular technology is restricted to rather narrowly specialized applications, as welding shields, and it would not be fully suitable for use in personal optical devices as sunglasses, goggles, etc. It is well known to those skilled in the art that twisted nematic devices suffer, among other difficulties, from adverse birefringence effects. It would be also impossible to provide broad variety of desired colors and change of colors with the pair of polarizers, as was already mentioned hereinabove. It is, therefore, obvious to those skilled in the art that device as described by Belgorod will need fundamental improvements in the light transmission range and in availability of broad color selection. Another field in which the aforementioned technology may be improved is its electronics driving scheme. Belgorod perceives the twisted nematic liquid crystal material to be an instantaneous (peak) responding material while in fact it is a rather slow material that responds only to rms, not peak voltages. Therefore, according to a time (duty cycle) driving scheme, as taught by Belgorod, a device (i.e. TN LC) will not switch as described.

Another type of liquid crystal technology, being now considered for utilization in this field, was first described by Heilmeier in U.S. Pat. No. 3,551,026 and later by many others as Bloom et al., etc. These teachings introduced application of specific class of dyes, known as pleochroic (or dichroic) dyes. By dissolving them into liquid crystal mixtures and by fabrication of devices including hereinabove, new type of color switching displays was achieved, now known as guest-host displays (further GH). However, as is well known to those skilled in the art, devices of this type suffer from a serious drawback in that, at best, the homogenously aligned dye molecules will absorb only 50% of the light incident upon the device, thereby resulting in poor display contrast.

Further improvement in GH technology was attained with the teaching of Taylor et al. in U.S. Pat. No. 3,833,287 by introduction of helical structure into the liquid crystal layer. The purpose of this helical molecular structure is to ensure that no matter what the orientation of the electric vector of the incident light, there will be a dye molecule at some distance between the spaced substrates with its long axis parallel to the vector to effect absorption. Thus, absorption of 90% or more of the incident light can be effected. Still further improvements in this GH type of display, commonly known to those skilled in the art as the phase-change GH, have been achieved and reported by many, to date, specifically in improvement of the color contrast, i.e. in widening of the range between end points of low and high transmission of incident light.

The construction and operation of guest-host type electro-optical information display devices are well known, as also shown by Ushiyama in U.S. Pat. No. 4,241,339, Suzuki et al. in U.S. Pat. No. 4,257,682 and by Tocashi in U.S. Pat. No. 4,266,859. Further progress in the use of guest-host phase-change complex mixtures are reported, among others, by Coates and Gray in U.S. Pat. No. 4,145,114, Sethofer et al. in U.S. Pat. No. 4,414,131, Funada et al. in U.S. Pat. No. 4,383,738, Huffman in U.S. Pat. No. 4,530,572 and by Mochizuki et al. in European Pat. No. 0 173 581. Use of GH technology in liquid crystal sunglasses is reported by Jinguu in Japanese Pat. No. 61-26021 (A).

It is well understood by those skilled in the art that guest host technology and, especially, its phase-change modification may bring considerable advantage over the twisted nematic mode in the field of light protection eyewear. The most significant factors are: variety of possible colors and variable density changes of hereinabove, elimination of optically disturbing birefringence effects, etc. However, it is also well known that prevailing effort in phase-change GH field has been directed mainly towards the needs of information displays. This means that all existing devices and mixtures have been designed to exhibit steep and well defined electro-optical saturation curve, i.e. with the shortest possible distance between the threshold ($V_{TH}$) and saturation ($V_{SAT}$) voltages. These values, however, are not acceptable for optical lens of the present invention, which requires shallow saturation curve. Also the customary values of $V_{TH}$ in present devices are not suitable for the lens of present invention, being either too low or too high.

Another limitation of the presently used GH devices for the purpose of present invention are their light scattering stages as described, among others, by Taylor et al. and Mochizuki et al. in their aforementioned patents. Taylor teaches that a "storage" effect appears when the molecular structure assumes a helix shape after removal of electric field. This stage is turbid and scatters light. Mochizuki describes two basic stages in GH phase-change devices. First is a focal-conic stage (F), when the system is in its quiescent stage and is scattering the incident light. The system becomes clear at homeotropic-nematic (H) stage while the peak voltage is applied. Existence of such a light scattering stage in an optical lens of the present invention would be highly undesirable. There is yet another optically scattering stage that occurs at the end of cholesteric to nematic transition, called dynamic scattering stage (D). Jinguu in his aforementioned teaching does not take into account either these shortcomings or the need for changes in the phase change guest-host formulation, including chiral materials.

Another limitation of the prior art in the field of liquid crystal sunglass eyewear design is that teaching of complementary and effective electronic driving circuits has not been fully comprehensive. Drawbacks of Belgorod's electronic design have been mentioned hereinabove while none other teaching contains any description of such.

Still another limitation of the prior art in the field of liquid crystal sunglass eyewear is lack of information about optical lens design which would conform with the latest fashion trends. Belgorod teaches that the glass lens with attached polarizers on both sides is of curved shape, other sources show glass lens with the flat surface. It will be exceedingly costly and impractical to mass produce curved glass liquid crystal eyewear TN lenses while flat surface lenses will not be acceptable as a consumer product.

What is still needed, however, is a design of an optical device which will not only retain the present state-of-the-art in eye protection and optical clarity, but in addition will incorporate effectively automated variable color and darkness of the lens. This variable color and variable darkness lens must be capable of automatically responding, either rapidly or gradually as conditions warrant or the user specifies, to every immediate change of light intensity conditions. Introduction of such a device is needed to combine two or more functionalities into a multipurpose lens, which will serve effectively and safely under a broad range of light conditions. It is clear that substantial changes in the operating mode of the state-of-the-art liquid crystal optical devices must be made to accommodate aforementioned requirements. The reason for this is that liquid crystal application in personal optics brings about a completely new field of technology. It is also clear that a completely novel type of—preferably lightweight plastic—curved lens housing of the optical lens must be developed to accommodate aesthetic requirements of the fashion consumer product. It is further clear that a novel and effective electronic driving circuit must be developed in order to accommodate the aforementioned specified lens operating requirements within variable light intensity and atmospheric conditions. Consequently, much room remains for improvement in this field.

SUMMARY OF THE INVENTION

Accordingly, it is an object of the invention to provide a sunlight protective optical device that incorporates the ability to vary both chromatic color and color density, and which corresponds exactly to the changes of ambient light conditions.

Another object of the invention is to provide liquid crystal variable color density optical lens, containing a novel liquid crystal layer of optical clarity that reacts either rapidly or gradually, depending on conditions or as the user has specified, to all changes of light intensity in the visible spectrum, be they broad or minute, without optical scattering, typical for state-of-the-art devices.

Still another object of the invention is to provide an embodiment of a liquid crystal variable color density optical lens wherein a liquid crystal optical layer is enclosed and specifically aligned in the plastic optical housing and connected to an integrated electronic driving system.

A further object of the invention is to provide a novel composition of a liquid crystal optical layer which will provide optical clarity of light transmission in all stages of electro-optical saturation and will be well suited for outdoor use, extreme lighting conditions and broad changes in the temperature.

Another object of the invention is to provide a broad range of color density within a liquid crystal optical lens, including the actual color changes (e.g. orange or yellow to dark brown, dark gray, dark purple etc.), this phenomenon being dependent only upon changes in the wavelength and intensity of light in the visible spectrum.

Still another object of the invention is to provide an appropriate plastic housing for the curved shaped lens, inside surface alignment and fabrication methods of thereof.

Still another object of the invention is to provide an integral electronic driver for the operation of the liquid crystal optical lens, consisting of an appropriate photoelectric detector with a variable voltage generator, square wave generating driver circuit, power source and connectors.

Briefly, a preferred embodiment of the present invention is an optical lens adapted to provide a preprogrammed response to changes in ambient light conditions. The specific embodiment of the lens for the preferred immediate use is in improved ski goggles in which the improved lenses replace traditional and the state-of-the-art color change sunglass lenses. The lenses are of a liquid crystal variety using the novel guest-host phase change type liquid crystal system with electronic control to assure constant optical clarity of the light transmission and to determine the coloration and color density of the lenses, thus affecting their transmissivity of light to the eye of the user. The light sensor and optical control portions of the invention cause the lenses to change color and darken or lighten in response to changes in the ambient light so as to insure maximum visibility and eye comfort for the user.

An advantage of the present invention is that the optical lenses are capable of extremely rapid alterations of color and color density in response to changes in ambient light.

Another advantage of the present invention is that alterations in color density and color of the lenses may be preprogrammed for specific utilizations.

A further advantage of the present invention is that the devices will utilize curve-shaped plastic lenses which are less expensive and lighter than glass lenses.

Yet another advantage of the present invention is that the entire control apparatus, including power source, for the invention may be easily carried in standard eyeglass or goggle frames.

A still further advantage of the present invention is that alterations in color and color density may be reversed in a manner which is as rapid as the initial changes.

Still another advantage of the present invention is that alterations in color and color density may be reversed also in a manner which is gradual and progresses in very short increments of an available voltage scale while maintaining throughout optical clarity, without occurrences of optical scattering.

These and other objects and advantages of the present invention will become clear to those skilled in the art upon review of the following specification and the appended claims.

BEST MODE OF CARRYING OUT THE INVENTION

The present invention is a variable color/variable color density optical system adapted for usage with optical lenses of various shapes, types and uses. This optical device operates utilizing a layer of liquid crystal/dye system embedded in the lens and controlled by an external electronic control circuitry, all of the present invention. The control circuitry is activated by sensing of the ambient light which allows it to alter the alignment of the molecules within the liquid crystal/dye layer, thus altering the transmissivity and visible color appearance of the lens. Expected uses of the invention will lie in any field where it is desirable to have a rapid and/or carefully predictable and controlled alteration of the color transmissivity of a lens in response to changes in the ambient light.

Figure 1:
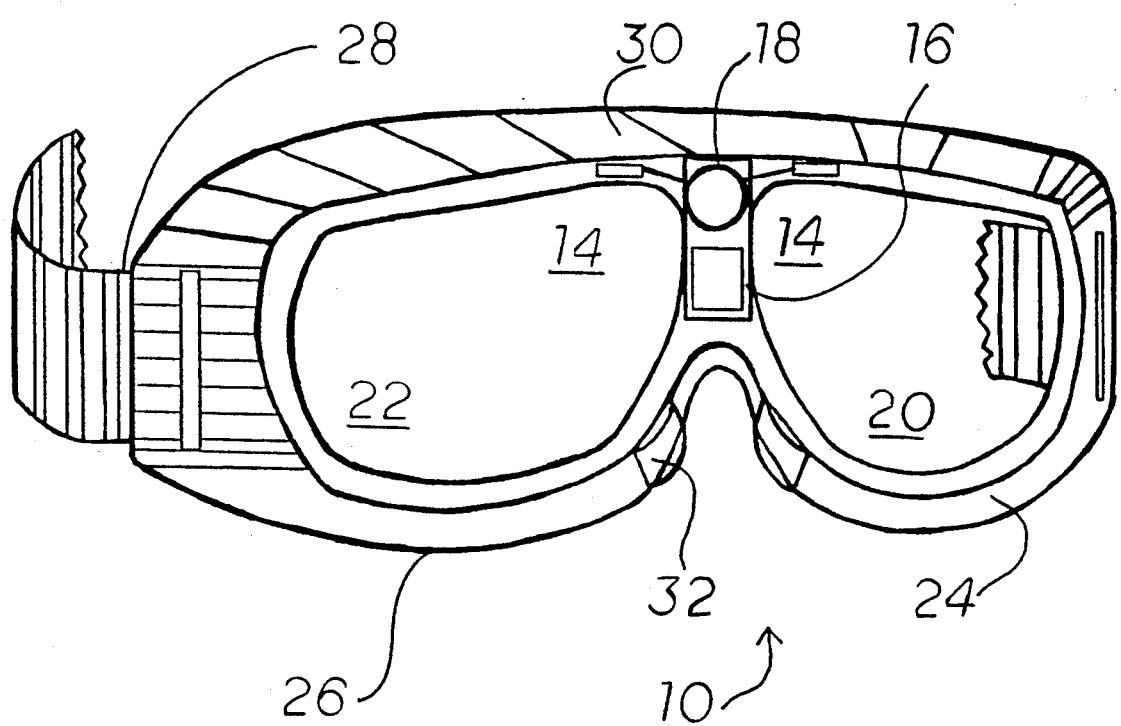
FIG. 1 is a perspective view of variable color/variable color density optical goggle device according to a preferred embodiment of the present invention.

Referring now to FIG. 1, a preferred embodiment of the variable color/variable color density optical system is shown in a preferred configuration as an optical goggle or sunglasses device. The optical system 10 is illustrated in the perspective view of FIG. 1, and referred to therein by the general reference character 10, as being installed within the optical goggle device 12. In the preferred embodiment, the optical goggle device 12 is a pair of conventional ski goggles which are similar to those utilized presently, with the alteration of including the optical system 10. It will be clear to those skilled in the art that a ski goggle embodiment is presented for illustration purposes only, as any other type of eyewear can be accommodated.

The optical system 10 includes three primary components which operate together in order to cause the differentials in color transmissivity. The first and largest of the components is a lens element 14 which includes the liquid crystal/dye material. The orientation of the liquid crystal molecules within the lens element 14 is altered by a control component 16 which delivers electrical signals to the phase change guest-host mixture of the present invention. The control component 16 receives input from a light sensor component 18 which responds to alterations in the ambient light and sends varying signals to the control component 16.

In the preferred embodiment illustrated in FIG. 1, the lens element 14 is in the form of a left lens 20 and a right lens 22, corresponding to the eyes of the user. The left and right lenses 20 and 22 are supported within a goggle frame 24 which also includes a peripheral shield 26 in the case of the ski goggle embodiment in order to protect the eyes and the inside of the lens from blowing snow or other material intrusions. The ski goggles 12 are held in position on the user's head by an attachment strap 28. Intermediate the left lens 20 and the right lens 22, the goggle frame 24 includes a central panel 30 which is located just above the bridge of the nose when in use. The central panel 30 provides a mounting position for the control component 16 and the light sensor 18. The optical goggle device 12 illustrated in FIG. 1 further includes a pair of nose pads 32, which are optional. The nose pads 32 aid the comfort of the user and keep the goggles in position.

Figure 2:
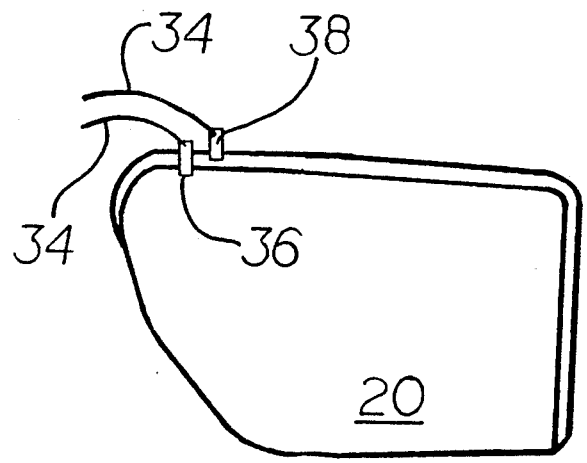
FIG. 2 is a front plan view of a portion of the right lens element, showing the manner in which the lens element is connected to the electronics.
Figure 3:
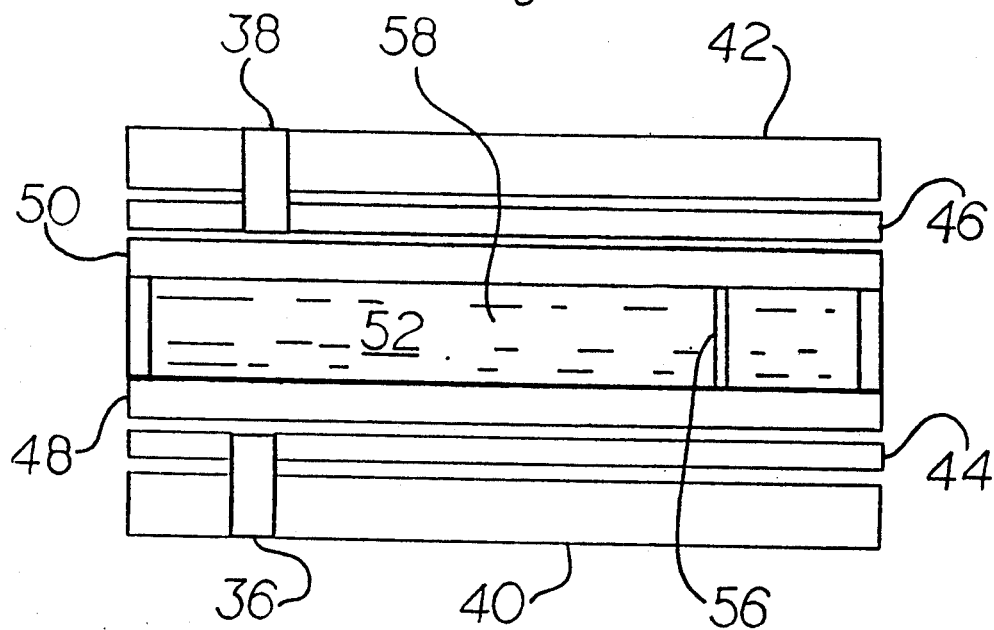
FIG. 3 is a cross sectional view, taken along line 3—3 of FIG. 2, showing the components of the lens element.

FIG. 2 illustrates one of the lens elements 14, in this case the left lens 20, in a partial front plan view. In this illustration it may be seen that the lens element 14 is connected to a pair of conductive conduits 34 by way of a first electrical connector 36 and a second electrical connector 38. Conductive conduits 34 extend from the electrical connectors 36 and 38 to the control component 16. The manner in which the electrical connectors 36 and 38 attach to the lens element 14 is best understood from the view of FIG. 3, a not-to-scale and a not curve-shaped illustration of the cross section of the lens element 14. As can be seen in the illustration of FIG. 3, the lens element 14 is formed in a series of distinct layers from front to back. The lens element 14 is substantially symmetrical in construction with layers repeating on both sides. The illustration is completely out of scale with respect to the thickness of the layers but it is necessary to accomplish this in order to have some of the layers be visible. For the ease of illustration, the figure is not presented in the curved shape, as necessary for an actual device.

The first external layer at the front, for conventional description, edge of the lens element 14 is a first substrate layer 40. A second substrate layer 42 is provided as the rearmost layer of the lens 14. The first and second substrate layers 40 and 42 are formed of conventional lens material, such as glass or plastic which are utilized in a typical lens. In the preferred embodiment 10, the first and second substrate layers 40 and 42 are formed of an appropriate, optically clear polymer (such as Polycarbonate) and each has a thickness of about 30 mils.

Moving inward, the next layers are a first conductive layer 44 (front) and a second conductive layer 46 (rear). In this case, the first conductive layer 44 is connected to the first electrical connector 36 and receives electrical signals therefrom while the second conductive layer 46 is connected to the second electrical connector 38. The first and second conductive layers 44 and 46 are typically formed of a mixture of indium and tin oxide (ITO) and are placed upon the interior surface of the respective first and second substrate layers 40 and 42 by a form of any customary deposition. Typically, the first and second conductive layers 44 and 46 will have a thickness of approximately 200 angstroms.

Situated inward from the conductive layers 44 and 46 are a first alignment layer 48 and a second alignment layer 50 which abut respectively against the first and second conductive layers 44 and 46. The construction of the first and second alignment layers and materials to achieve the same for state-of-the-art technology is well known to those skilled in the art. Preferred materials include polyvinyl alcohol, polyamide and methyl cellulose. Typically, either homogenous (parallel), tilted or homeotropic (perpendicular) alignments of liquid crystal molecules towards the substrate can be achieved. Both the first and second alignment layer (44 and 50) have an approximate thickness of 300 angstroms.

A central cavity 52 is formed intermediate the first and second alignment layers 48 and 50. A peripheral seal 54 extends completely about the boundaries of the central cavity 52 between the first and second alignment layers 48 and 50 in order completely to seal the volume of the central cavity 52. In the case of a large lens element 14, such as that utilized in the ski goggle device 12 of the preferred embodiment 10, a plurality of internal spacers 56 may be provided within the central cavity 52 in order to prevent collapse. The internal spacers 56 may be formed of a transparent material such as glass fibers. The internal spacers 56 serve a purpose similar to that of pillars between floors of a building. That is, they allow free flow of materials around the pillars while preventing the adjacent surfaces from contacting each other.

The central cavity 52 is filled with a liquid crystal medium 58 which contains the liquid crystal elements which are the heart of the invention. The liquid crystal medium 58 is evenly distributed and completely fills the entire central cavity 52. In an embodiment such as the preferred ski goggle device 12 and sun glasses the preferred thickness of the central cavity 52 is approximately 10 to 15 microns. The liquid crystal medium 58 provides the mechanism by which the transmissivity of the lens element 14 is modified by the response of a multitude of individual aligned liquid crystal molecules 59 (See FIGS. 6 and 7) within the liquid crystal medium 58 to altering electrical changes within the first and second conductive layers 44 and 46. Similarly, a plurality of dye molecules 62 align in different fashions to produce color variations.

The liquid crystal optical layer 58 is a novel negative image phase guest-host liquid crystal mode, and is comprised of three portions, as a modification of a state-of-the-art phase change system. As discussed above, liquid crystal devices known to those skilled in the art as twisted nematic mode will not be suitable for lens operation of present invention. A simple guest-host type of LC device (i.e. combination of liquid crystal and dichroic dyes) is also not suitable.

Figure 4:
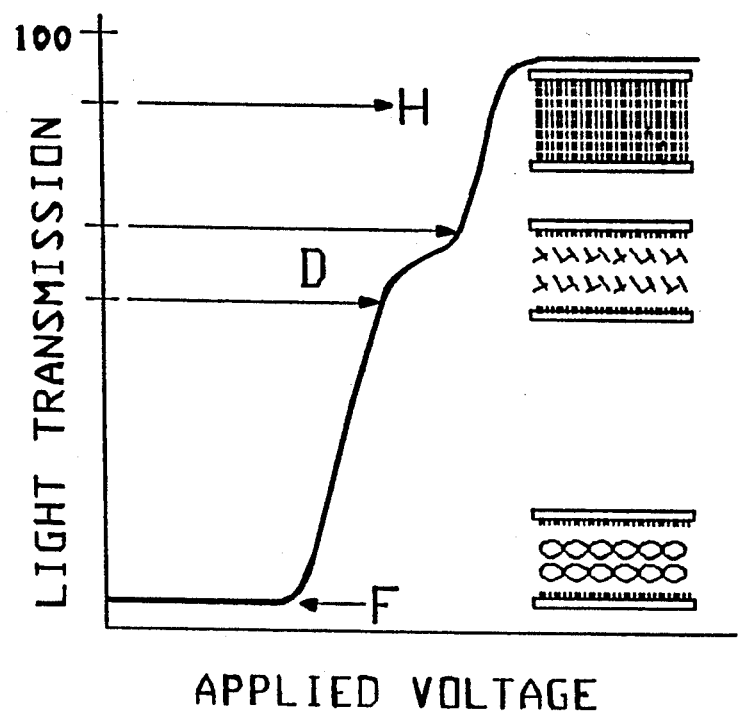
FIG. 4 is a schematic electro-optical saturation curve for a negative guest-host phase change device, typical for the state-of-the-art information display devices.

The family of liquid crystal electro-optical displays, known to those skilled in the art as phase-change Guest-Host devices, forms the background for the operation of the lens element 14 of the present invention. These displays have had potential utility for information display purposes such a digital clocks or watches, calculators and other instruments, providing that they can display a sharp transitions from electro-optical threshold to electro-optical saturation. It is well known that higher concentrations of chiral additives, which are needed for substantial increase of the contrast of a device, i.e. those which induce helical twist of 270° or higher, have a strong tendency to form light scattering focal conic structures at the surface interface with phase change mixtures at the quiescent state, i.e. when applied voltage is below the electro-optical threshold (as shown in FIG. 4—stage F). These structures can be acceptable or even desired for certain applications such as reflective information displays where additional light scattering can increase visual contrast. However, for the purposes of the present invention, which requires optically clear transmission, this phenomenon will not be acceptable.

Another optical disturbance, shown in FIG. 4—stage D, takes place in a typical phase change guest-host device about at 80% on the saturation curve within the range of 0.2 to 0.4 volts. It is characterized as a dynamic optical scattering and can be noticed as a cloud, or haze, quite visible by, and disturbing to, a naked eye. This particular phenomenon has been occasionally described in the literature, however, it was never considered detrimental to the proper function of an information display. The reason for this is that reflective information display is being switched from "off" to "on" state (and vice versa) within about 100 msec, which leaves only few miliseconds for the duration of the described stage D. However, this particular optical disturbance is not acceptable for the operation of the lens of the present invention, as it will often coincide with immediate light intensity conditions and provide occasional unwanted blur within the lens. The last optical condition of a typical guest-host device, as shown in FIG. 4—stage H, is an optically clear state where all components of the phase change system are aligned parallel to the electric field and perpendicular to the lens substrates, i.e. they form a homeotropic nematic stage.

Figure 5:
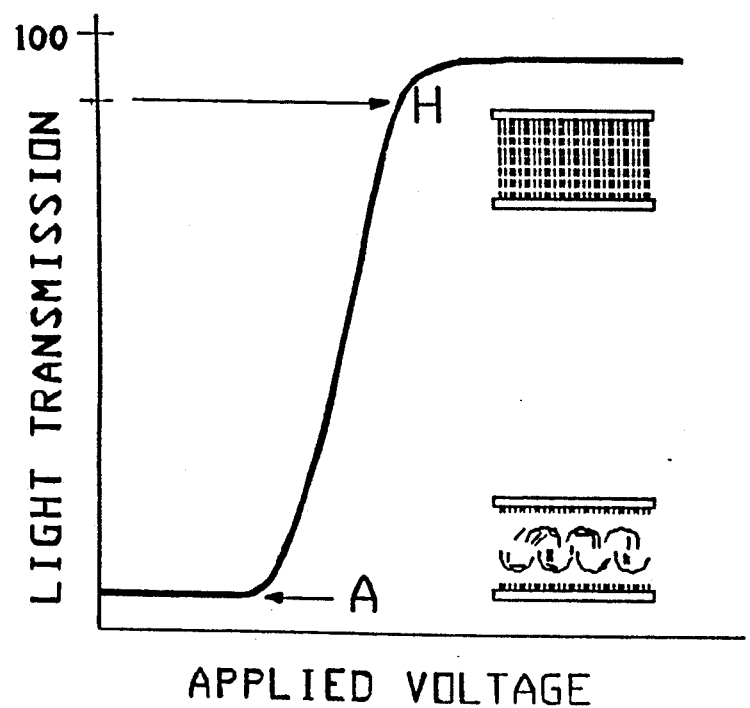
FIG. 5 is a schematic electro-optical saturation curve for a negative guest-host phase change device of the present invention, suitable for use in an optical lens.

It is, therefore, obvious that for the proper function of the lens 14 of the present invention, stages F and D, as shown in FIG. 4, had to be eliminated. FIG. 5 shows the desired mode of operation of the phase change guest-host system of the present invention. Quiescent state, stage A (i.e. where voltage is below an electro-optical threshold), is characterized by first several layers of the LC complex 58 being perpendicular to the substrate surfaces and then gradually changing into a system of helixes that run, generally, in parallel with the said surfaces. This aforementioned stage is optically clear and does not form disturbing focal conic structures. By a gradual increase of voltage, no dynamic scattering phase can be observed until the saturation voltage has been reached. At this point, the desired homeotropic stage H has been achieved. As shown in FIG. 5, any chosen point on the saturation curve produces clear transmittance of the light and clear vision for a wearer of the optical device of the present invention.

In order to achieve the mode of operation described in FIG. 5, two problems had to be solved. Firstly, the means to achieve optically clear "off" alignment of LC/dye complex had to be found and secondly, a novel host liquid crystal complex had to be formulated, especially including a proper host mixture and a proper chiral additive, in order to assure clarity of the optical transmission along the whole electrical operating range of the lens of the present invention.

Figure 6:
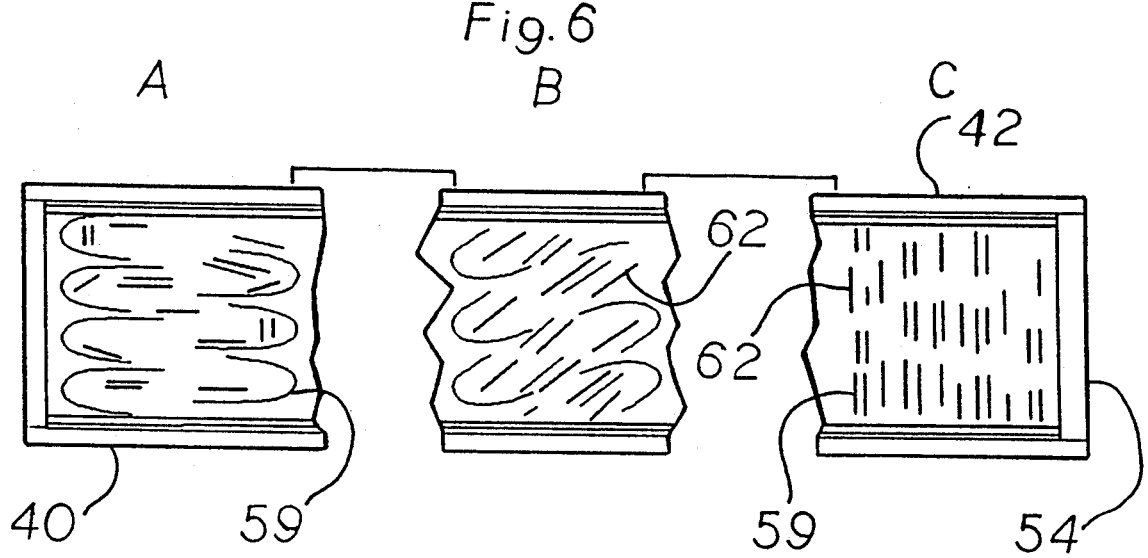
FIG. 6 is a schematic illustration of changes in molecular homogenous alignment of the liquid crystal optical layer (shown in both front and cross sectional fashion) from the electro-optical threshold voltage (a.) to the electro-optical saturation voltage (c.), through an intermediate voltage (b.) applied about midway between the threshold and saturation voltages.
Figure 7:
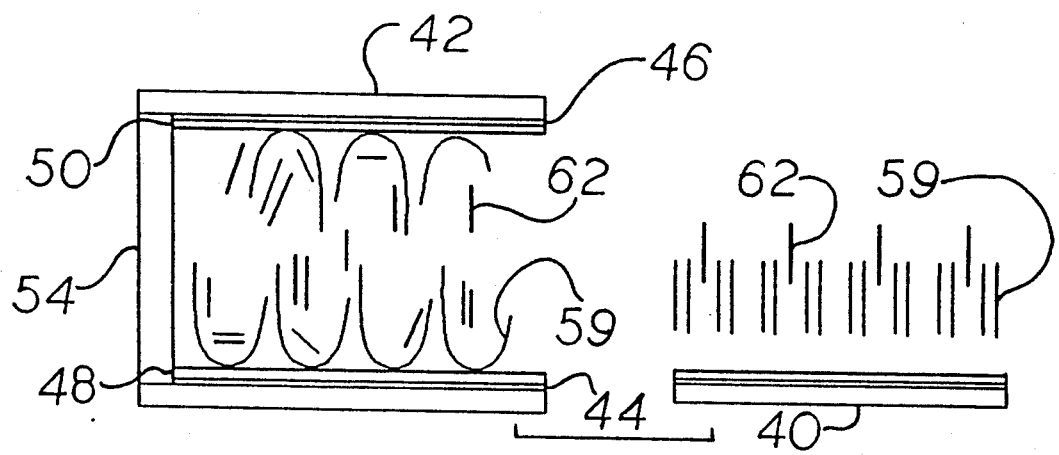
FIG. 7 is a schematic illustration of a preferred surface molecular alignment of the liquid crystal layer, the alignment being homeotropic with surface molecules aligning perpendicularly (90 degree tilt) to the lens substrate.

In order to illustrate a problem of surface alignment, we will explain actions of different alignments in FIG. 6 and FIG. 7. The most commonly used surface alignment at the interface of a substrate and liquid crystal complex is the homogenous alignment, i.e. where several surface LC layers are situated in parallel or at some angle with the substrate in the off state. In this case, as illustrated in FIG. 6A, a chiral addition forces the whole complex to form a helix of varying tightness, dependent upon cholesteric pitch and concentration, between two substrates, i.e. LC complex is in the cholesteric phase. Upon a gradual increase of electric field, molecules of the complex begin to straighten within the direction of the electric field, as illustrated in the FIG. 6B, where about 50% of peak voltage has been applied. The molecules of the LC complex are now exhibiting a physical movement and at some point, (at about 80% of the saturation), dynamic light scattering centers are formed due to change of direction of molecules 59 and 62, i.e. from parallel to perpendicular to the substrates. FIG. 6C illustrates the final phase where over 90% of the peak voltage had been already applied and LC complex has assumed homeotropic nematic phase, which produces optically clear transmission and minimum coloration due to well known properties of the dichroic dyes 62. It is possible to eliminate focal conic structure in the quiescent homogenous alignment by an accurate admixture calculation of chiral additive, however, it is not very practical as the precise dependence between cell thickness and chiral concentration exists and overall thickness uniformity within the cell becomes extremely critical.

A noticeable improvement is achieved within devices where surface treatment produces perpendicular, i.e. homeotropic alignment, as illustrated in FIG. 7. Several layers of the liquid crystal complex immediately adjacent to the surface assume perpendicular alignment to the plane of the substrate and force the groups of cholesteric helixes to run, generally, in parallel with the surfaces of substrates. According to a simplified model, the cholesteric helix can be perceived as a form of a tube, inserted within a device. It is obvious that upon the voltage ramp-up, the complex molecules 59 do not have to change general direction from parallel to perpendicular and consequently, formation of dynamic scattering centers should be diminished before true homeotropic nematic state H is reached. Our experiments proved this assumption to be correct. However, even though both "off" state focal conic structures and dynamic scattering have greatly diminished with introduction of the homeotropic alignment, they still remained present with the use of conventional and state-of-the-art host liquid crystal materials and chiral additives.

As it is well known to those skilled in the art, the substantial portion of phase change guest-host system, usually 92 to 99 percent by weight, is represented by an appropriately designed nematic liquid crystal mixture, also known as the host mixture 60, which is a determining factor of important electrical, optical and environmental properties. It is also well known that numerous and available types of liquid crystal materials exhibit various chemical, physical and optical properties. Some of these properties must be considered to be essential for the operation of all types of LC devices, such as an appropriate temperature working range, chemical and photo-chemical stability, etc. Other specific properties would be, however, important in different degrees for different particular applications. Among such properties are varying levels of electrical threshold, values of optical birefringence, viscosity, etc. During the research of the lens of the present invention, we have established that in order to eliminate unwanted optical disturbances, the host liquid crystal material must exhibit, besides required temperature range and stability, very low values of optical birefringence (delta n) combined with low electro-optical threshold (represented by high values of dielectric anisotropy, delta E). Another important requirement is to achieve a shallow but short, about 45°, electro-optical saturation curve, which is quite to the contrary to requirements for information displays where steep saturation curve is all but essential.

Such liquid crystal materials were found and are presented in the particular preferred embodiment of the host nematic liquid crystalline composition 60 for the purpose of the present invention. These compounds exhibit, besides required temperature range and chemical stability, all hereinabove described properties. They include trans isomers of 1,3-cyanophenyl dioxanes and cyclohexyl dioxanes, phenyl/cyclohexyl ester compounds and combined 1,3-dioxane and ester liquid crystalline components. Dioxanes are represented by both two and three ring, rod-like shaped molecules while such esters and dioxane-esters are three ring liquid crystal molecules of the same shape. Two ring molecules are present in amount of not less than 70 weight percent. Prolonged compounds, containing at least three rings and displaying high nematic to isotropic transitions, are present in amount of 15 to 30 weight percent of a host mixture.

In a particular embodiment of the host liquid crystalline compositions 60 for the purpose of the present invention, the suitable components are selected from the group of compounds set forth in Table 1, below in the concentration states. Ordinarily, only a subset of the components will be utilized in a given formulation. In the event that a large number of components are utilized, especially those having similar properties, it may be necessary to revise the applicable percentages downward to achieve a workable mixture.

TABLE 1

|  | Weight % |
| --- | --- |
| 5-ethyl-2-(4-pentylcyclohexyl)-1,3-dioxane | 5-25 |
| 5-ethyl-2-(4-heptylcyclohexyl)-1,3-dioxane | 5-25 |
| 5-propyl-2-(4-pentylcyclohexyl)-1,3-dioxane | 5-25 |
| 5-propyl-2-(4-heptylcyclohexyl)-1,3-dioxane | 5-25 |
| 5-ethyl-2-[4-(4-pentylcyclohexyl)cyclohexyl]-1,3-dioxane | 5-25 |
| 5-butyl-2-(4-cyanophenyl)-1,3-dioxane | 10-30 |
| 5-pentyl-2-(4-cyanophenyl)-1,3-dioxane | 10-30 |
| 5-hexyl-2-(4-cyanophenyl)-1,3-dioxane | 10-30 |
| 5-heptyl-2-(4-cyanophenyl)-1,3-dioxane | 10-30 |
| 5-propyl-2-[4-(4-pentylcyclohexyl)-phenyl]-1,3-dioxane | 1-25 |
| 5-propyl-2-[4-(4-heptylcyclohexyl)-phenyl]-1,3-dioxane | 1-25 |
| 4-methoxyphenyl-4-propylcyclohexane carboxylate | 1-25 |
| 4-ethoxyphenyl-4-propylcyclohexane carboxylate | 1-25 |
| 4-butyloxyphenyl-4-propylcyclohexane carboxylate | 1-25 |
| 4-methoxyphenyl-4-butylcyclohexane carboxylate | 1-25 |
| 4-ethoxyphenyl-4-butylcyclohexane carboxylate | 1-25 |
| 4-methoxyphenyl-4-pentylcyclohexane carboxylate | 1-25 |
| 4-pentylphenyl-4-pentylcyclohexane carboxylate | 1-25 |
| 4-propylphenyl-4-(4-propylcyclohexyl) benzoate | 1-10 |
| 4-cyanophenyl-4-(4-ethylcyclohexyl) benzoate | 1-10 |
| 4-cyanophenyl-4-(4-pentylcyclohexyl) benzoate | 1-10 |
| 4-cyanophenyl-4'-(5-propyl-1,3-dioxan-2-yl) | 1-10 |
| 4-cyanophenyl-4'-(5-butyl-1,3-dioxan-2-yl) | 1-10 |
| 4-cyanophenyl-4'-(5-pentyl-1,3-dioxan-2-yl) | 1-10 |

Typically, all above components with at least one aliphatic ring are represented by trans configuration. All attached linear aliphatic groups are normal.

Typically, the host liquid crystalline mixtures 60 used in the preferred embodiment 10 require specific characteristics which were discussed hereinabove and which will be illustrated even further when a complete liquid crystalline—chiral—dye complex will be introduced.

One liquid crystalline composition of the present invention is illustrated by means of the following example which is included for purposes of illustration rather than limitation:

EXAMPLE I

|  | Weight % |
| --- | --- |
| 5-ethyl-2-(4-pentylcyclohexyl)-1,3-dioxane | 10.0 |
| 5-ethyl-2-[4-(4-pentylcyclohexyl)cyclohexyl]-1,3-dioxane | 7.5 |
| 5-butyl-2-(4-cyanophenyl)-1,3-dioxane | 19.0 |
| 5-pentyl-2-(4-cyanophenyl)-1,3-dioxane | 13.0 |

-continued

| | Weight % |
|---|---|
| 5-hexyl-2-(4-cyanophenyl)-1,3-dioxane | 16.0 |
| 5-heptyl-2-(4-cyanophenyl)-1,3-dioxane | 13.0 |
| 5-propyl-2-[4-(4-pentylcyclohexyl)-phenyl]-1,3-dioxane | 7.0 |
| 5-propyl-2-[4-(4-heptylcyclohexyl)-phenyl]-1,3-dioxane | 5-25 |
| 4-butyloxyphenyl-4-propylcyclohexane carboxylate | 5-25 |
| 4-pentylphenyl-4-pentylcyclohexane carboxylate | 5-25 |
| 4-cyanophenyl-4-(4-pentylcyclohexyl) benzoate | 2.0 |
| 4-cyanophenyl-4'-(5-propyl-1,3-dioxan-2-yl) | 1.5 |
| 4-cyanophenyl-4'-(5-butyl-1,3-dioxan-2-yl) | 1.5 |
| 4-cyanophenyl-4'-(5-pentyl-1,3-dioxan-2-yl) | 1.5 |

The admixture shown in Example I exhibits melting point of about −35° C. (could not be frozen), clearing point (nematic to isotropic transition temperature) of 85° C., optical birefringence (delta n) of 0.10 and dielectric anisotropy (delta E) above +20. The electro-optical characteristics for regularly aligned twisted nematic cell with 10 to 12 micron spacing and with surface tilt angle of about 10° are as follows:

$V_{10}$ (10% saturation)=0.9 V
$V_{90}$ (90% saturation)=1.4 V
response times $T_{ON}$ and $T_{OFF}$ within 100 to 120 msec Preparation of the complex guest-host mixture 58 for the liquid crystal optical layer of the present invention must be further aided by admixture of 2 to 8% of a chiral (cholesteric) additive 61 which will thus become the another part of such a complex mixture. The chiral additives 61, when admixed into the nematic host, will produce a cholesteric helix of predetermined pitch in the hereinabove described mixture as it aligns within the optical lens in a predetermined direction. Predetermined directions in case of the lens of the present invention are, as described hereinabove, homeotropic boundaries between LC complex and both substrates' surfaces.

The commonly used chiral additives for the purpose of increasing contrast in reflective information type displays such as cholesteryl nonanoate or 4-cyano-4'-(2-methyl)-butylbiphenyl (CB-15) and many others, have not proved satisfactory in meeting requirements for operation of the optical lens of the present invention, namely in preventing optical scattering and focal conic structures. All of these conventionally used chiral additives exhibit rather tight cholesteric structure even in low concentrations and often, high values of optical birefringence, thus forming visible, light scattering centers on the homeotropic boundaries. These chiral compounds also force the helix to align and run between the substrates (FIG. 6) thus causing aforementioned dynamic scattering, especially when high optical birefringency and low dielectric anisotropy host materials are used. When observing the phase change transition under the microscope, one can clearly notice the original tight and almost circular focal conic patterns (stage F) to rearrange direction into a form, which has been described in the literature as a fingerprint structure (stage D), before reaching saturation homeotropic stage. Upon removal of voltage, the state-of-the-art system relaxes again into its quiescent tightly arranged and light scattering focal conic pattern F.

Therefore, what is additionally needed for the proper operation of the lens of the present invention, is a chiral additive which will have: a/ a rather loose cholesteric pitch of about 40 microns, b/ small value of optical anisotropy and, c / large positive dielectric anisotropy, requirements a/ and b/ being of absolute necessity. Such a class of chiral additives, possessing all three of aforementioned requirements is represented by optically active derivatives of 1,3-dioxane components. One example of such chiral additives is 5-(2-*methyl)butyl-2(4-cyanophenyl)-1,3-dioxane. This particular component, included for purposes of illustration rather than limitation, displays dielectric anisotropy (delta E) greater than +20, optical birefringence lower than 0.10 and cholesteric pitch is about 0.38 microns (comparing to 0.16 microns of commonly used cyanobiphenyl CB-15). When used in a proper concentration with nematic host composition of the present invention and with homeotropic alignment, boundaries at the mixture/surface interface produce desired A alignment, as illustrated in FIG. 5. When observing this type of phase change under the microscope, one can notice original quiescent state represented by long and wide regular cylindrical patterns, which is presumed to be a helical structure A as described in FIG. 5. This structure does not produce optically disturbing light scattering. Upon increasing of voltage, one can observe gradual narrowing and shortening of aforementioned patterns but without directional rearrangement and without any dynamic scattering stage, until their complete disappearance at the saturation voltage, i.e. when transition from cholesteric to nematic/homeotropic phase is completed. The important factor is the absence of the dynamic scattering "fingerprint" structure D, as described in FIG. 4.

While calculating the preferred amount of the chiral additive to be placed into an LC complex of the present invention, one has to consider required contrast and take into account the particular thickness of the cavity within the lens. Another consideration is to achieve required shallow (45°), yet short slope of the saturation (i.e. contrast vs. voltage) curve. The preferred concentration of hereinabove type of chiral additive into the host nematic mixture of the present invention is about 3.6% by weight in a 12 micron lens device, which is presented here as means of illustration rather than limitation.

The final step in the composition of the guest-host liquid crystalline complex 58 is provided by the introduction of at least 0.3 weight percent, preferably 1.5 to about 4 weight percent of a dichroic dye, or a mixture of dichroic dyes. Preferably, dichroic dyes are used, having an order parameter (S) greater than 0.65 as determined by conventional measurement techniques.

Use and mode of operation of appropriate dichroic dyes is one of important factors for guest-host type of operation, both in basic and phase change modes and it is well known to those skilled in the art. There are several types of dichroic dyes known and used in different types of electro-optical devices, such as azo dyes, Schiff-base type dyes, anthraquinone dyes, etc. However, considering the prevailing outdoor usage of the lens of the present invention, chemically and photochemically stable anthraquinone and like dyes would be preferred. Colors of available and suitable dichroic dyes include blue, purple, red and yellow-orange. By choosing an appropriate combination of these dyes, a mixture of desired color absorption and a shade of same will be provided. A preferred technique of color mixing is the subtractive method which includes preparation and calculation of complementary subtractive colors cyan, magenta and yellow and their subsequent proportional admixture for desired color.

The resulting color with maximum absorption in the visible light spectrum and the percentage of light transmission at maximum and minimum of applied voltage are measured and corrected by use of visible range spectrophotometer for a lens of the standard thickness and fabricated of preferred liquid crystalline host and chiral materials, dyes and plastic housing material.

Another preferred method to provide variable color density of the lens, herein incorporating actual color changes, is application of a colored (bright yellow or orange) front and rear plastic substrate layers 40 and 42. While clear front and rear lens substrates 40 and 42 provide near colorless state at maximum transmission, use of colored substrates provides light coloration at maximum transmission and actual color change at increasing absorption.

Still another preferred method of providing variable color density to the lens, herein incorporating actual color changes, is adding admixture of non-dichroic, brightly colored yellow or orange dyes, such as members of the coumarin group, to the liquid crystal medium 58, as it is well known to those skilled in the art. As these dyes do not display transmission along one molecular axis, (they are often spherically non-linear) use of non-dichroic (isotropic) dyes provides light coloration at maximum transmission, and actual color change at increasing absorption.

Figure 10:
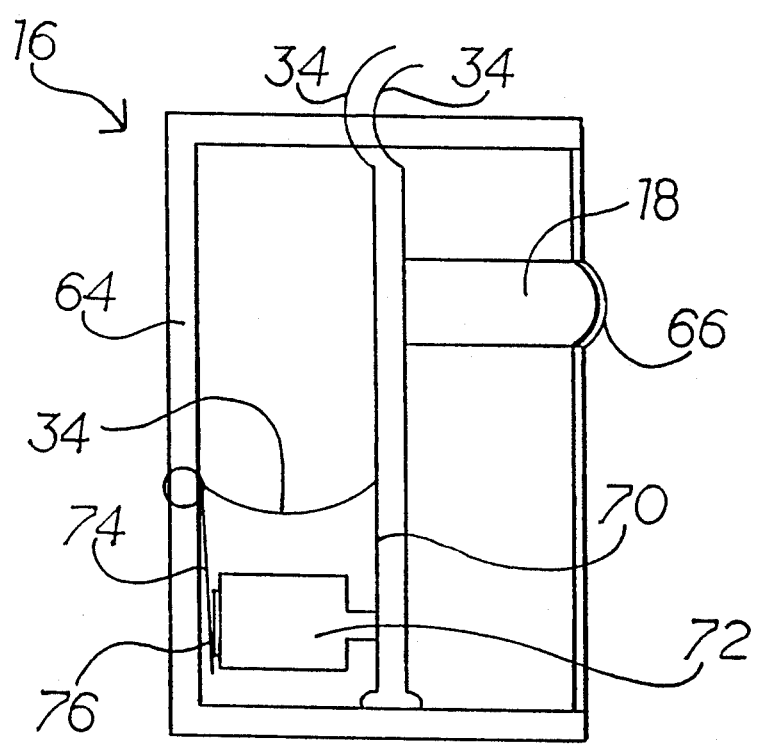
FIG. 10 is a cross sectional view, taken along line 4—4 of FIG. 1, showing the elements of the control component.

Referring now to FIG. 10, the control component 16 is illustrated in a cross sectional view. In this illustration it may be seen that the control component to include several individual elements which operate together to provide electrical signals through the conductive conduits 34 to the first electrical connector 36 and the second electrical connector 38.

In the preferred embodiment of ski goggles 12 and sunglasses it is necessary to protect the control component 16 from the elements such as snow, ice and wind. The control component 16 is therefore provided with a protective casings 64. In the front of the protective casing 64 is provided a sensor aperture 66 which is optically clear to the front such that a light sensor 68 may face forward from the goggle 12. The light sensor 68, of any of several conventional types, is selected to have a good linear response within the range of light intensities expected to be encountered in the particular environment. There are several types of light sensors, which are suitable for use in aforementioned products, such as photoresistors, photodiodes, solar cells, etc.

The light sensor 68 is directly connected to the electronics contained on a circuit board 70 which is enclosed within the protective casing 64. The circuit board 70 includes circuitry, as will be described hereinafter with respect to FIGS. 8 and 9, which provides the appropriate response to the input from the light sensor 68 and delivers control signals through the conductive conduits 34 to the first electrical connectors 36 and the second electrical connector 38 on the lens element 14.

Electrical power for the various elements of the circuit board 70 and the light sensor 68 is provided by a battery 72 which is also enclosed within the protective casing 64. The battery is accessible from the exterior of the protective casing 64 through a battery access door 74. On the interior of the battery access door 74 is provided an electrical contact 76 in order to provide a complete circuit with the battery 72 and the circuit board 70.

In the optical goggle device 12 of the preferred embodiment the control component 16 is directly attached to the goggle frame 24 by mounting the protective casing 64 directly to the central panel 30 of the goggle frame 24. This positioning is desirable because it provides the best mounting point for a single sensor 68 to react to changes in the ambient light which will impact upon the left lens 20 and the right lens 22.

In other embodiments of the present invention of optical system 10 the control component 16 will be utilized in similar positions on eyeglasses or other elements wherein it is desirable to alter the transmissitivy of a lens. In the case of eyeglasses or specialized sunglasses it is expected that it may be possible to further miniaturize the control component 16 such that it may be mounted in a small slot within the eyeglass frame itself. Furthermore, in sunglasses, or other optical devices which are not likely to be subjected to harsh environmental conditions, the protective casing 64 may be eliminated or minimized. In some instances it may be also possible to mount the battery and circuit board components in a position more remote from the light sensor 68.

Figure 8:
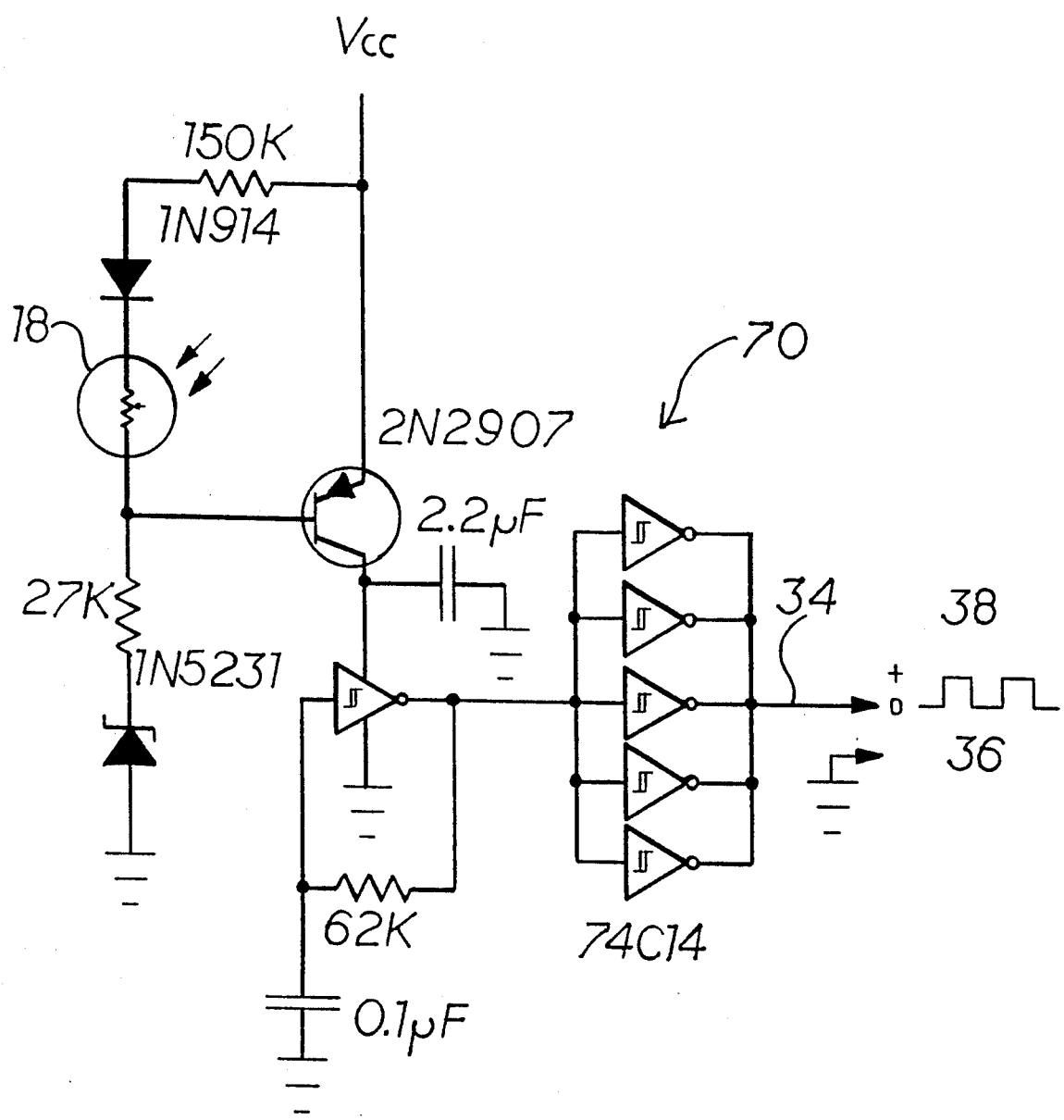
FIG. 8 is a schematic illustration of a simple electronic circuit, producing DC square wave output and capable of driving the entire system.
Figure 9:
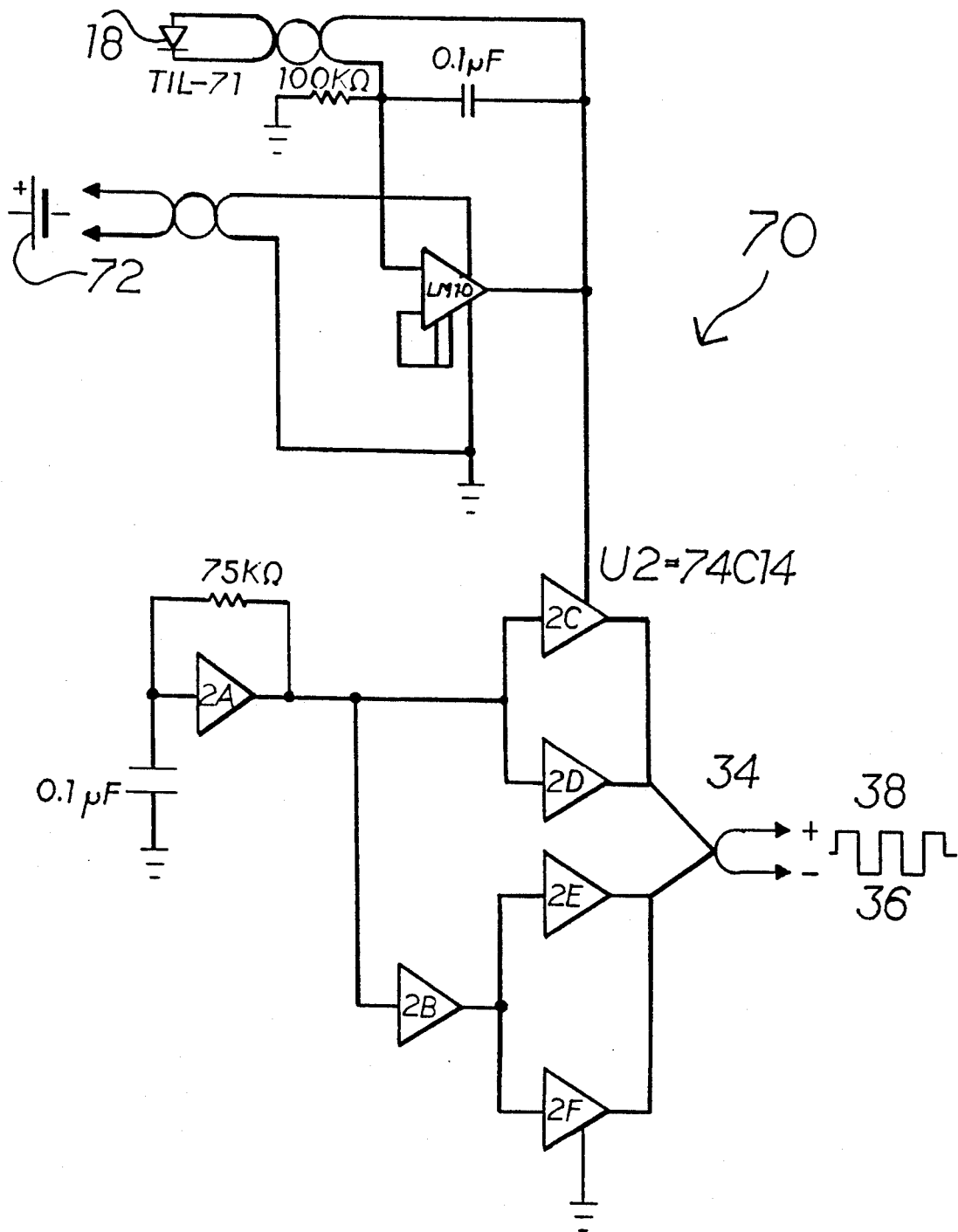
FIG. 9 is a schematic illustration of a preferred embodiment of simple electronic circuit, producing AC square wave output and capable of driving the entire system.

The illustrations of FIG. 8 and FIG. 9 show a pair of alternate circuits which may be utilized in the circuit board 70 of the present invention in order to provide proper control signals to the first electrical connector 36 and the second electrical connector 38 in order to achieve the desired alternations in the liquid crystal liquid crystal complex medium 58. Important parts of an electronic drivers of present invention are suitable oscillator/driver circuits and regulator circuits as illustrated, for example purposes in FIGS. 8 and 9. It is well known to those skilled in the art that liquid crystal devices require AC or simulated AC voltage input for longevity of their operations. It is also well known that square wave form voltage input is advantageous for such devices due to its considerable rms values. The preferred frequency for the lens of the present invention will be within 32 to 100 Hz, but not less than 32 Hz in order to avoid flicker.

FIG. 8 shows 74C14 hex inverter being used as a square wave oscillator and an LC lens driver. One of its six inverters, along with the 0.1 Mfd capacitor and 62K resistor, form the oscillator and the other five inverters are wired in parallel to drive the lens. Because of the characteristics of the 74C14, the oscillator's duty cycle will remain 50/50 even if a supply voltage is changed. This oscillator drives the other five inverters, who's combined outputs drive the LC lens. The 74C14 switches from ground to $V_{CC}$. If this supply voltage is changed, the output voltage of the 74C14 will change accordingly. FIG. 8 also shows a regulator circuit, which consists of 2 diodes, 2 resistors, the photo sensor and the 2N2907 PNP transistor. Top lead is the emiter, middle one is the base and the lower is the collector. Transistor action is such that small currents in the base cause larger currents to flow from emiter to collector. The diodes and resistors provide 2 current paths. One to turn the 2N2907 on, and one to turn it off. In low intensity light conditions, the photo sensor is high resistance and almost no current flows through it, nor through the 150K and 1N914. The 2N2907 is then on because its base lead is being pulled toward ground through the 27K resistor and the 1N5231. As the light increases, the photo sensor resistance decreases and pulls the base lead more positive and this causes less current to flow from emiter to collector. The more light, the less current flows into the oscillator/driver circuit. Less current develops less voltage and the output voltage to the lens goes down. As the light decreases, more current flows thus causing the output voltage to increase. This aforementioned circuit provides a pulsating DC output.

FIG. 9 illustrates still improved circuit for the operation of the lens of the present invention as the same oscillator/driver circuit 74C14 (hex inverter) has been corrected to provide a true AC output. It operates as follows: When square wave oscillator section 2A switches high, both 2C and 2D switch low, driving one side of the LC lens. 2B also switches low, causing 2E and 2F to switch high, driving the other side of the LC lens. When section 2A switches low, 2C and 2D switch high, and 2B switches high and drives 2E and 2F low. This reverses the potential on the LC lens. As in the circuit of FIG. 8, the peak output voltage of this circuit will follow the supply voltage provided to it. FIG. 9 also shows a regulator circuit that uses a low power operational amplifier/reference integrated circuit LM10. This IC has its reference voltage generator connected to pin 3 (positive input) and is otherwise configured as a non-inverting amplifier. The output voltage—pin 6—will go to whatever value is required to make the voltage at pin 2 (negative input) equal to pin 3, because of the feedback network. The output voltage is a feedback to pin 2 via a voltage divider consisting of the TIL-71 and 100K resistor. The TIL-71 is a photo diode and its resistance changes with changes of light intensity. The more light intensity, the lower is the resistance of the diode. Less resistance in this part of the circuit lowers the amplifier's gain and therefore, lowers the output voltage. Less light, on the other hand, causes the resistance of the diode to increase and simultaneously, to increase the output voltage to LC lens. The 0.1 Mfd capacitor slows down the response of the circuit to reduce flicker. The voltage generated at pin 6 of the regulator circuit provides the supply voltage for the oscillator/driver circuit.

Considering the above illustrated circuits, it is clear that device shown in FIG. 9 will be more preferable for the lens operation because it produces true AC square wave input while device shown in FIG. 8 produces DC square wave input with residual straight DC offset. There are numerous photo sensors 68 known to those skilled in the art, such as photoresistors, phototransistors, etc., which may be employed in the present invention. The examples circuitry shown in FIG. 8 shows specific application of a photoresistor type of sensor while FIG. 9 shows application of a photo diode. Photoresistors display their sensitivity peak very close to that of the human eye, i.e. at about 550 nm in the visible light region, therefore, the type of sensor as shown in FIG. 8 will be more preferable for use with the lens of the present invention. For this type of sensor it is important that the voltage divider circuit on the circuit board 70 allows, due to variable resistance of the photoresistor, full voltage to be transmitted at little or no outside light intensity, while incoming voltage to the lens is completely blocked at bright sunshine or under similar high light intensity conditions. The variable resistance photoresistor also detects and translates intermediate stages of outside light intensity into variable voltage outputs. A direct result of the above is variable color density (and color changes) of the lens 14 with its maximum darkness at bright sunshine, its maximum transmission (lightness) during inadequate outside light conditions, and variable stages of lens darkness in direct dependence upon changing intensity of outside illumination. The precision and fine grading of the voltage output for different conditions, and according to user's requirements, will be also aided by addition of a suitable algorithm, incorporated into the electronic system.

The desired power source 72 for the overall system of the present invention will be a lithium-type battery of an appropriate size, shape and adequate capacity, capable of supplying power to last for at least one year of an uninterrupted operation.

It is desirable that photo detecting, voltage regulating and square wave generating circuits, along with other useful additions such as programmable algorithm, step-up voltage, etc., shall be incorporated into gate-array circuit or small dedicated chip 70.

The manufacture of a lens element 14 of the preferred optical system 10 may be accomplished as follows.

Plastic lens materials for the substrate layers 40 and 42 are selected and cut into the desired size and shape from a sheet of plastic material (such as Lexane, Rohm and Haas Plexiglas, butyrate, etc.), the thickness of which is preferably in the range of 0.5 to 0.75 cm (0.020 to 0.030 inch). The lens material is selected either to be clear or to display light yellow, amber or similar coloration and should contain appropriate ultraviolet light absorbers with effective wavelength cutoff within the range of 380 to 460 nm.

The inside surfaces of the plastic substrate layers 40 and 42 are then covered with the thin (typically 100–500 angstroms), continuous and transparent conductive layers 44 and 46, typically a mixture of indium/tin oxides. The next step in the fabrication of the lens element 14 is the formation of the surface alignment layers 48 and 50. This is accomplished by a treatment where the group of substrates is submerged, in an appropriate holder, into a 0.05 to 0.5% solution of lecithin or octadecyl dimethyl-(3-trimethoxysilyl)-propyl ammonium chloride (DMOAP) in methanol, the temperature of which is maintained within the range of 25° to 30° C. After few minutes they are removed from the solution and blown dry with a stream of compressed air, or preferably, dry nitrogen. Other methods as for example, spinning aforementioned solutions upon the substrates surfaces, may be employed.

The next step involves the temperature treatment ("curing") of the alignment layer by storing the components at the temperature of 80° C. for at least 2 hours with continuous stream of dry air or preferably, dry nitrogen. This "cold" process is very important as it prevents formation of grazing and other types of optical defects that would be introduced into and onto plastic substrates by customary high temperature curing process.

The various components are then brought together to define the central cavity 52 by bonding the edges of the first layers (40, 44, 48) to those of the second layers (42, 46, 50) with the peripheral seal 54. The example of peripheral seal 54 is an ultraviolet curing sealing material, such as Norland NOA 68. The sealing material is placed upon one of the plastic substrates. This peripheral seal 54 is introduced by appropriate means, familiar to those skilled in the art, such as screen printing, and is interrupted in one place for each lens 14 for a separation in the width of about 0.25 cm (0.100 inch), to create a fill hole. The internal spacers 56 are then applied to the surface, prior to sealing, using appropriate tooling such as a "puff chamber" to insure their even distribution. The internal spacers 56 control the thickness of the liquid crystal central cavity 52 and thus some of the optical properties of the final device. Spacers 56 ranging in size from 6 to 20 microns are commercially available providing a wide range of choices to the designer. This invention will preferably use spacers 56 in the range of 12 to 15 microns.

After placement of the spacers 56 the fabrication proceeds with a sealing process where the first substrate 40, with first conductive layer 44 and the first alignment layer 48 formed thereon, is aligned with the corresponding set of second layers 42, 46 and 50, with the peripheral seal 54 and the spacers 56 therebetween.

The components are pressed together in the way that both surfaces abut tightly against evenly distributed spacers 56, but do not touch each other, thus forming the desired central cavity 52 of predesigned thickness. The sealing material of the peripheral seal 54 is then subjected to curing by ultraviolet radiation, typically in the range of 320 to 380 nm. The UV light may be provided by a mercury lamp or xenon bulb or any of a number of commercially available sources such as "Opticure Light Gun" by Norland Products.

The final step in fabrication of the lens element 14 is the introduction of the liquid crystal medium 58 into the cavity 52. The host mixture 58, as illustrated in Example 1. with preferred chiral additives and dichroic dyes, as also described hereinabove, is placed in a narrow trough which itself is placed into a vacuum chamber. A group of empty lenses 14 is arrayed over the trough in an appropriate holder with the opening in the peripheral seal 54 (fillhole) facing down. The chamber is evacuated to approximately 50 millitorr or less and, after about 45 minutes, the empty lenses are lowered in such a way that fillhole touches the surface meniscus of the aforementioned mixture 58. The chamber is then gradually refilled with air or preferably, with dry nitrogen, in the course of 5 to 10 minutes. Gradually increasing pressure forces the liquid crystal medium 58 into the central cavity 52. After removal of the filled lens elements 14 from the chamber, the opening in the peripheral seal 54 is covered with appropriate sealing material and properly cured. Once the electrical connectors 36 and 38 are attached to the respective conductive layers 44 and 46 the liquid crystal variable color density lens 14 of the present invention becomes operational.

The fabrication method described above provides an certain plastic materials for the substrate layers 40 and 42. However, number of different polymers can provide similar optical clarity and other useful properties for this purpose, such as allyl diglycol carbonates, polycarbonates, polystyrenes, polysulfones, polyether sulfones, polyesters and others, familiar to those skilled in the art.

Another characteristic of the lens 14 is that mostly, specific curvature is required for its shape. Therefore, the preferred method to economically fabricate such a lens and also to minimize the possibility of optical distortions induced by the curvature is described hereinafter by means of the following example, which is included for purposes of illustration rather than limitation.

Figure 11:
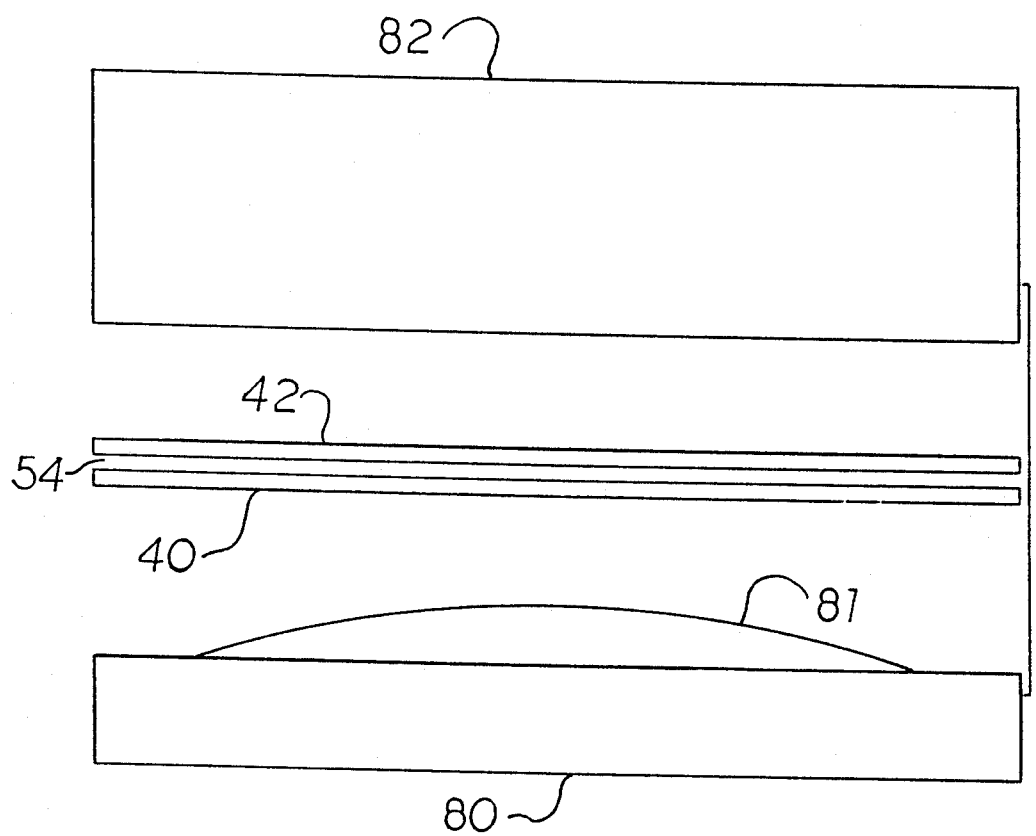
FIG. 11 is a schematic illustration of a preferred mode of producing a cylindrically or otherwise shaped lens of the present invention.

The principle of the method is to design first layers and second layers of the lens 14 to be of different lengths, corresponding to their appropriate lengths when curved. All processing of the aforementioned parts, up to the sealing stage, is done in arrays, on the flat surface in accordance with the above fabrication process. However, the sealing step is then performed on a specially designed form, selected for the specific application to be curved into the desired lens shape, as illustrated in FIG. 11. Processed parts, i.e. upper substrate 42 and lower substrate 40 with an interrupted ring (fill hole) of appropriate adhesive (in this case preferably pressure sensitive adhesive) and spacers 54 are placed upon a surface 80 with desired curvature shape 81. A block of a rigid, yet still elastic and collapsible material 82 is placed overhead both parts 42 and 40 and enough pressure (over 170 in lb) is then applied by means of mechanical pressure, air pressure, etc. After removal of the pressure (about after 3-4 hours), the resulting lens of the present invention assumes desired curvature in shape with even thickness of internal cavity. Then filling and sealing processes are provided, as described hereinabove.

The aforementioned preferred process introduces some amount of stress birefringence into the cell rather than creating thickness variations within the cell in general and, into the liquid crystal medium, in particular.

As used herein the term "lens" encompasses any element through which the desired wavelengths of electromagnetic radiation may pass but which prohibits passage of other relevant forms of energy and/or matter. More specifically, it is used to mean a panel which permits light passage but restrains liquid flow and provides a structural member. This differs from the more common usage of the term in that there is no requirement that any refraction, such as focusing or diffusion, take place during the passage of the radiation through the "lens". Thus, for the purposes of this disclosure and the following claims, a uniform window pane would qualify as a "lens" while it could be stated that it would not under the commonly accepted definition. It is not intended to restrict the invention in any way as to curvature, thickness or uniformity of thickness as to the "lens" elements since it is envisioned that the invention will be viable with wide variations in all of these properties.

INDUSTRIAL APPLICABILITY

The operation of optical system 10 of the present invention is best understood by consideration of the various examples presented in FIGS. 6, 7, 12 and 13. These illustrations schematically show the manner in which the liquid crystal layer both macroscopically and microscopically responds to alterations in the ambient light level.

Figure 12:
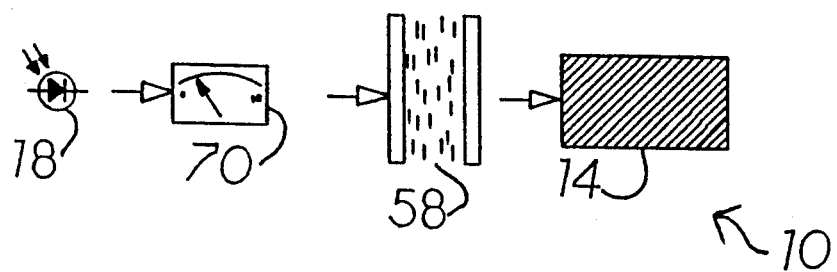
FIG. 12 is a schematic illustration of the reaction of an optical device embodying features of the present invention, shown as it would operate in high intensity light, such as full sunshine. The lens component is shown from both a side cross-section and front orientations.
Figure 13:
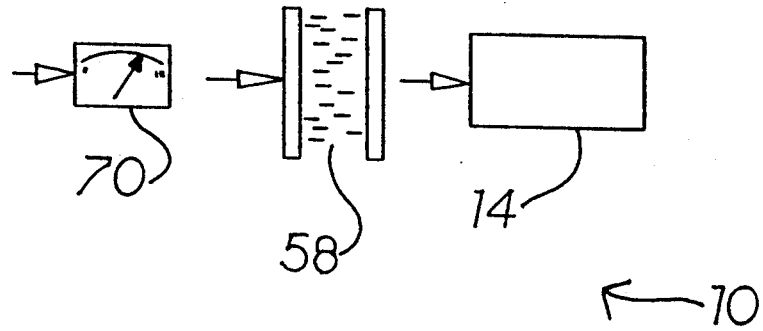
FIG. 13 is an illustration complimentary to that of FIG. 12, showing the reaction of the device to low light intensity conditions, such as overcast.

FIGS. 12 and 13, respectively, illustrate the manner in which the optical system 10 of the present invention responds to bright lighting conditions such as full sunshine or dark lighting conditions such as heavy overcast. In the case of full sunshine, FIG. 12, the light sensor 68 deliver electrical analog signals to the circuit board 70 corresponding to a high density of ambient light, i.e. minimum or null voltage. The circuit board 70 then sends appropriate signals to the conductive layers 44 and 46 within the lens element 14 which caused the individual liquid crystal molecules 59 within the liquid crystal medium 58 to align themselves in a manner as shown in FIG. 5, phase A. In this alignment the phase change guest-host mixture of the present invention is maximally absorptive of incoming radiation and result in minimum transmission of light to the user's eyes. The alignment of the liquid crystals 59 within the medium 58 is schematically illustrated in the side view portion of FIG. 12, while the viewpoint of the user, showing maximum opacity is illustrated in the front view portion of FIG. 12.

Similarly, FIG. 13 illustrates the response of the optical system 10 of the present invention to low light conditions such as heavy overcast. In this illustration it may be seen that the light sensor 68 will send to the circuit board 70 signals corresponding to a low level of ambient light, i.e. maximum voltage. The circuitry of the circuit board 70 will then deliver signals to the first and second conductive layers 44 and 46 which cause the liquid crystal molecules within the liquid crystal medium 58 to align perpendicularly to the surfaces of the substrate layers 40 and 42. In this manner a minimum of absorption of the ambient light is accomplished by the liquid crystal dye mixture and the maximum transmissivity occurs. The alignment of the complex mixture is schematically illustrated in the side view of FIG. 13 while the viewpoint from the user, showing the maximum transmission of the lens 14, is shown in the front view.

An example of surface alignment is illustrated in FIG. 7 as a preferred embodiment of the present invention. This structure may be accomplished by forming the alignment layers 48 and 50 of materials such as lecithin, DMOAP, etc. (see hereinabove). When this material is utilized as the construction material for the alignment layers 48 and 50 the several layers of liquid crystal molecules adjacent to the surface 59 will align such that they have a surface molecular tilt angle of approximately perpendicular or 90° to the substrate surface. This arrangement, in conjunction with the host and chiral LC materials of the present invention, results in the cholesteric helix running in parallel with the substrate surfaces instead of between them, as would be the case in FIG. 6. This preferred arrangement of the helix results in a faster reaction to introduction of the electric field and in the conjunction with aforementioned LC materials of the present invention prevents formation of disturbing optical scatterings. This preferred structure is schematically illustrated in FIG. 7 both in a side view and a cross-sectional surface view.

As seen from the above examples and illustrations, the optical system 10 of the present invention is adaptable for usages where varying degrees of transmissivity and color selection are desirable. Presently expected embodiments include, in addition to the ski goggles 12, eyeglasses, shields, glare screens on CRT terminals, windows and the like. It is expected that the technology of the present invention will be adaptable to nearly any sort of situation in which variable color transmissivity of light and optical clarity are desired in response to ambient conditions.

In light of the above, and especially in light of the rapid color response and the compact unitary design of the optical system 10, it is expected that the invention according to the preferred and alternate embodiments will enjoy widespread commercial utility and industrial applicability.

I claim:

1. An electro-optical variable color variable transmissivity lens assembly comprising:
    a polymer lens housing, including exterior lens panels encompassing a central cavity, said panels being adapted to have various degrees of curvature;
    a composition of a phase change guest-host liquid crystal/dyes complex, possessing positive dielectric anisotropy, situated and aligned within said cavity of the polymer lens housing;
    a first alignment layer and a second alignment layer being provided on the substrate surfaces of said lens panels adjacent to said cavity, said alignment layers being provided with homeotropic alignment that is achieved by a "cold" process that will prevent mechanical and optical deformations of said lens panels during the lens operation; and
    electronic photodetecting and oscillating/driving circuit system means, for operation of the said electro-optical lens to alter the alignment of the composition in response to changes in light conditions.

2. The assembly of claim 1 wherein said electronic photodetecting and oscillating/driving circuit means includes
    a power source in the form of a high capacity battery;
    a control component including one or more light sensors;
    a light sensing voltage regulator circuit; and an oscillator/driver circuit.

3. The assembly of claim 2 wherein
    each said light sensor is a photodiode;
    said light sensing voltage regulator circuit incorporates a low power operational amplifier which operates by providing a peak voltage at minimal levels of lighting conditions and, conversely, limits the voltage supply at bright light conditions;
    said oscillator/driver circuit includes a 74C14 hex inverter utilized as a square wave generator with 50/50 duty cycle output regardless of voltage supply level, said hex inverter being incorporated into the circuit in such a way as to produce true alternating current output without residual direct current values.

4. An electro-optical variable color variable transmissivity lens assembly comprising:
    a polymer lens housing, including exterior lens panels encompassing a central cavity, said panels being adapted to have various degrees of curvature;
    a composition of a phase change guest-host liquid crystal/dyes complex, possessing positive dielectric anisotropy, situated and aligned within said cavity of the polymer lens housing,
    electronic photodetecting and oscillating/driving circuit system means, for operation of the said electro-optical lens to alter the alignment of the composition in response to changes in light conditions;
    the composition of the liquid crystal/dye complex of the phase change guest-host system being selected to assume an optically clear state of cholesteric phase in a quiescent state, within said lens cavity, without exhibiting focal conic light scattering structures;
    the composition of the liquid crystal/dye complex of the phase change guest-host system being selected to undergo a gradual transformation from its quiescent cholesteric state to a homeotropic nematic state upon voltage transition from zero to maximum voltage and vice versa, without producing dynamic scattering stages; and
    the composition of the colored liquid crystal/dye complex of the phase change guest/host system being selected to reach the optically clear nematic homeotropic stage at a saturation voltage ranging from 4 to about 6.5 VAC.

5. The assembly of claim 4 wherein the composition of the colored liquid crystal/dye complex of phase change guest-host system includes
    a nematic host mixture formed exclusively of nematic liquid crystalline materials exhibiting positive dielectric anisotropy;

one or more chiral liquid crystalline additives exhibiting positive dielectric anisotropy; and
a guest mixture formed of dichroic dye materials.

6. The assembly of claim 5 wherein
said nematic host mixture is composed of at least 90% by weight of first nematic components which exhibit both low optical birefringence and high positive dielectric anisotropy, while the remainder of said nematic host mixture is composed of second nematic components which do not exhibit low optical birefringence but do exhibit moderately high values of positive dielectric anisotropy, so as to aid in the production of a shallow and short electro-optical saturation curve; and
said first nematic components include at least 23% by fractional weight of long, three ring components;
said first nematic components include at least 70% by fractional weight of two ring components having lower melting temperatures than said long three ring components and exhibiting very low optical birefringence combined with extremely high positive dielectric anisotropy in order to aid in formation of said saturation curve, to aid in providing contrast and elimination of optical distortions and in establishment of a proper temperature range.

7. The assembly of claim 6 wherein said nematic host mixture is formulated of components selected from the group of liquid crystalline materials set forth in the following table, with the preferred ranges in weight percent being set forth for each component, in the event that such component is selected;

| # | | |
|---|---|---|
| 1 | 5-ethyl-2-(4-pentylcyclohexyl)-1,3-dioxane | 5–25 |
| 2 | 5-ethyl-2-(4-heptylcyclohexyl)-1,3-dioxane | 5–25 |
| 3 | 5-propyl-2-(4-pentylcyclohexyl)-1,3-dioxane | 5–25 |
| 4 | 5-propyl-2-(4-heptylcyclohexyl)-1,3-dioxane | 5–25 |
| 5 | 5-ethyl-2-[4-(4-pentylcyclohexyl)cyclohexyl]-1,3-dioxane | 5–25 |
| 6 | 5-butyl-2-(4-cyanophenyl)-1,3-dioxane | 10–30 |
| 7 | 5-pentyl-2-(4-cyanophenyl)-1,3-dioxane | 10–30 |
| 8 | 5-hexyl-2-(4-cyanophenyl)-1,3-dioxane | 10–30 |
| 9 | 5-heptyl-2-(4-cyanophenyl)-1,3-dioxane | 10–30 |
| 10 | 5-propyl-2-[4-(4-pentylcyclohexyl)-phenyl]-1,3-dioxane | 1–25 |
| 11 | 5-propyl-2-[4-(4-heptylcyclohexyl)-phenyl]-1,3-dioxane | 1–25 |
| 12 | 4-methoxyphenyl-4-propylcyclohexane carboxylate | 1–25 |
| 13 | 4-ethoxyphenyl-4-propylcyclohexane carboxylate | 1–25 |
| 14 | 4-butyloxyphenyl-4-propylcyclohexane carboxylate | 1–25 |
| 15 | 4-methoxyphenyl-4-butylcyclohexane carboxylate | 1–25 |
| 16 | 4-ethoxyphenyl-4-butylcyclohexane carboxylate | 1–25 |
| 17 | 4-methoxyphenyl-4-pentylcyclohexane carboxylate | 1–25 |
| 18 | 4-pentylphenyl-4-pentylcyclohexane carboxylate | 1–25 |
| 19 | 4-propylphenyl-4-(4-propylcyclohexyl) benzoate | 1–10 |
| 20 | 4-cyanophenyl-4-(4-ethylcyclohexyl) benzoate | 1–10 |
| 21 | 4-cyanophenyl-4-(4-pentylcyclohexyl) benzoate | 1–10 |
| 22 | 4-cyanophenyl-4'-(5-propyl-1,3-dioxan-2-yl) | 1–10 |
| 23 | 4-cyanophenyl-4'-(5-butyl-1,3-dioxan-2-yl) | 1–10 |
| 24 | 4-cyanophenyl-4'-(5-pentyl-1,3-dioxan-2-yl) | 1–10 |

8. The assembly of claim 5 wherein
said chiral cholesteric liquid crystalline additives are represented by low optical birefringence (about 0.1) and high (over +20) positive dielectric anisotropy compounds which exhibit moderate cholesteric pitch (about 0.40 microns), namely compounds of a general formula 5-(2-*methyl)-alkyl-2(4-cyanophenyl)-1,3-dioxane, where *methyl represents an optically active center and where the expression "alkyl" represents an aliphatic group.

9. The assembly of claim 8 wherein
said chiral additive is 5-(2-*methyl)-butyl-2-(4-cyanophenyl)-1,3-dioxane.

10. The assembly of claim 5 wherein
the composition of the phase change guest-host complex is in accordance with the following example by weight percent of each component:

| # | | |
|---|---|---|
| 1 | 5-ethyl-2-(4-pentylcyclohexyl)-1,3-dioxane | 9.50 |
| 5 | 5-ethyl-2-[4-(4-pentylcyclohexyl)cyclohexyl]-1,3-dioxane | 7.11 |
| 6 | 5-butyl-2-(4-cyanophenyl)-1,3-dioxane | 18.00 |
| 7 | 5-pentyl-2-(4-cyanophenyl)-1,3-dioxane | 12.32 |
| 8 | 5-hexyl-2-(4-cyanophenyl)-1,3-dioxane | 15.16 |
| 9 | 5-heptyl-2-(4-cyanophenyl)-1,3-dioxane | 12.32 |
| 10 | 5-propyl-2-[4-(4-pentylcyclohexyl)-phenyl]-1,3-dioxane | 6.63 |
| 11 | 5-propyl-2-[4-(4-heptylcyclohexyl)-phenyl]-1,3-dioxane | 3.79 |
| 14 | 4-butyloxyphenyl-4-propylcyclohexane carboxylate | 1.89 |
| 18 | 4-pentylphenyl-4-pentylcyclohexane carboxylate | 1.89 |
| 21 | 4-cyanophenyl-4-(4-pentylcyclohexyl) benzoate | 1.89 |
| 22 | 4-cyanophenyl-4'-(5-propyl-1,3-dioxan-2-yl) | 1.43 |
| 23 | 4-cyanophenyl-4'-(5-butyl-1,3-dioxan-2-yl) | 1.43 |
| 24 | 4-cyanophenyl-4'-(5-pentyl-1,3-dioxan-2-yl) | 1.43 |
| 25 | 5-(2-*methyl)-butyl-2-(4-cyanophenyl)-1,3-dioxane | 2.84 |
| 26 | dichroic dye mixture | 2.37 | said chiral additive is 5-(2-*methyl)-butyl-2-(4-cyanophenyl)-1,3-dioxane; and
said guest mixture is designated in the above tabulation as the dichroic dye mixture and is selected from the dyes of order parameter above 0.65, exhibiting desired coloration and chemical resistance.

11. The assembly of claim 5 wherein
said nematic host mixture contains at least 10% by weight of extremely low melting point, extremely low optically birefringent components (in the range of 0.03 to 0.05), combined with medium positive dielectric anisotropy of about +7, to aid in elimination of optical distortions.

12. The assembly of claim 5 wherein
said nematic host mixture includes components in the weight proportions set forth in the following table:

| Material # | | |
|---|---|---|
| 1 | 5-ethyl-2-(4-pentylcyclohexyl)-1,3-dioxane | 10.0 |
| 5 | 5-ethyl-2-[4-(4-pentylcyclohexyl)cyclohexyl]-1,3-dioxane | 7.5 |
| 6 | 5-butyl-2-(4-cyanophenyl)-1,3-dioxane | 19.0 |
| 7 | 5-pentyl-2-(4-cyanophenyl)-1,3-dioxane | 13.0 |
| 8 | 5-hexyl-2-(4-cyanophenyl)-1,3-dioxane | 16.0 |
| 9 | 5-heptyl-2-(4-cyanophenyl)-1,3-dioxane | 13.0 |
| 10 | 5-propyl-2-[4-(4-pentylcyclohexyl)-phenyl]-1,3-dioxane | 7.0 |
| 11 | 5-propyl-2-[4-(4-heptylcyclohexyl)-phenyl]-1,3-dioxane | 4.0 |
| 14 | 4-butyloxyphenyl-4-propylcyclohexane carboxylate | 2.0 |
| 18 | 4-pentylphenyl-4-pentylcyclohexane carboxylate | 2.0 |
| 21 | 4-cyanophenyl-4-(4-pentylcyclohexyl) benzoate | 2.0 |
| 22 | 4-cyanophenyl-4'-(5-propyl-1,3-dioxan-2-yl) | 1.5 |
| 23 | 4-cyanophenyl-4'-(5-butyl-1,3-dioxan-2-yl) | 1.5 |
| 24 | 4-cyanophenyl-4'-(5-pentyl-1,3-dioxan-2-yl) | 1.5 |

13. A variable color density optical device comprising:
a first variable transmissivity lens element;
a second variable transmissivity lens element;

a frame element supporting the first and second lens elements in a position corresponding to the left and right eyes of the user;

a control component, mounted in association with the frame element, the control component including one or more light sensors for sensing the intensity of light in the vicinity of the first and second lens elements, regulator circuitry adapted to regulate the voltage level in response to said light sensor, square wave generation circuitry adapted to generate square wave alternating current in response to regulated direct current level input provided by said regulator circuitry, conductive means for carrying said signals to the first and second lens elements, and power source means for supplying electrical power to said sensors and said circuitry;

wherein each of the first and second lens elements includes a central cavity enclosing a composition of a phase change guest-host liquid crystalline/dye complex mixture, said guest-host composition being characterized by positive dielectric anisotropy and being aligned by homeotropic boundaries created by first and second alignment layers formed on each of the lens elements; and wherein each lens element includes a conductive layer juxtaposed about said central cavity and electrically connected to said conductive means, such that said electrical signals respectively delivered to said conductive layers of the lens elements cause an alternation in the alignment of said composition system from an optically clear quiescent cholesteric stage, gradually and without light scattering occurrences, to another optically clear end state, in the nature of a homeotropic nematic alignment, in response to variations in the light intensity sensed by said sensors.

14. The device of claim 13 wherein each of the first and second lens housing elements is a substrate, constructed of an appropriate polymer so as to help maintain optical clarity and to maintain a uniform thickness throughout the said curved central cavity.

15. The device of claim 13 wherein said composition includes a host component primarily composed of nematic liquid crystalline materials with a small percentage of cholesteric liquid crystalline materials added thereto to urge the preferred type of helical alignment; and a guest component composed of one or more dichroic dye materials.

16. The device of claim 15 wherein said cholesteric liquid crystalline materials are characterized by low optical birefringence (about 0.1) and high dielectric anisotropy (greater than +20) and which exhibit moderate cholesteric pitch (approximately 0.40 microns), namely, compounds of a general formula 5-(2-*methyl)-alkyl-2(4-cyanophenyl)-1,3-dioxane, where "*methyl" represents an optically active center and where "alkyl" represents an aliphatic group.

17. The device of claim 15 wherein said preferred composition is comprised as set forth in the following table, according to weight percentage:

| | |
|---|---|
| 5-ethyl-2-(4-pentylcyclohexyl)-1,3-dioxane | 9.50 |
| 5-ethyl-2-[4-(4-pentylcyclohexyl)cyclohexyl]-1,3-dioxane | 7.11 |
| 5-butyl-2-(4-cyanophenyl)-1,3-dioxane | 18.00 |
| 5-pentyl-2-(4-cyanophenyl)-1,3-dioxane | 12.32 |
| 5-hexyl-2-(4-cyanophenyl)-1,3-dioxane | 15.16 |
| 5-heptyl-2-(4-cyanophenyl-1,3-dioxane | 12.32 |
| 5-propyl-2-[4-(4-pentylcyclohexyl)-phenyl]-1,3-dioxane | 6.63 |
| 5-propyl-2-[4-(4-heptylcyclohexyl)-phenyl]-1,3-dioxane | 3.79 |
| 4-butyloxyphenyl-4-propylcyclohexane carboxylate | 1.89 |
| 4-pentylphenyl-4-pentylcyclohexane carboxylate | 1.89 |
| 4-cyanophenyl-4-(4-pentylcyclohexyl) benzoate | 1.89 |
| 4-cyanophenyl-4'-(5-propyl-1,3-dioxan-2-yl) | 1.43 |
| 4-cyanophenyl-4'-(5-butyl-1,3-dioxan-2-yl) | 1.43 |
| 4-cyanophenyl-4'-(5-pentyl-1,3-dioxan-2-yl) | 1.43 |
| 5-(2-*methyl)-butyl-2-(4-cyanophenyl)-1,3-dioxane | 2.84 |
| dichroic dye mixture | 2.37 |

* * * * *